United States Patent [19]

Michel et al.

[11] Patent Number: 4,468,520

[45] Date of Patent: Aug. 28, 1984

[54] 3-CYANO-INDOLES AS CARDIOSELECTIVE AGENTS

[75] Inventors: Helmut Michel, Mannheim; Wolfgang Kampe, Heddesheim; Roland Ofenloch, Lorsch; Karl Dietmann, Mannheim; Gisbert Sponer, Laudenbach, all of Fed. Rep. of Germany

[73] Assignee: Boehringer Mannheim GmbH, Mannheim, Fed. Rep. of Germany

[21] Appl. No.: 288,075

[22] Filed: Jul. 29, 1981

[30] Foreign Application Priority Data

Aug. 8, 1980 [DE] Fed. Rep. of Germany ....... 3030047

[51] Int. Cl.³ .................... C07D 209/04; A61K 31/40
[52] U.S. Cl. ..................................... 424/274; 548/505; 548/492; 548/493; 548/495
[58] Field of Search ....... 260/326.16, 319.1, 326.13 R; 424/274; 548/492, 493, 495, 504

[56] References Cited

U.S. PATENT DOCUMENTS

3,699,123 10/1972 Seeman et al. ............. 260/326.14 R
4,076,829 2/1979 Kampe et al. ........................ 424/274
4,080,463 3/1978 Troxler ................................. 424/274

FOREIGN PATENT DOCUMENTS

1905881 9/1969 Fed. Rep. of Germany ....................... 260/326.16
2830211 2/1979 Fed. Rep. of Germany ....................... 260/326.16

*Primary Examiner*—Donald G. Daus
*Assistant Examiner*—G. Hendricks
*Attorney, Agent, or Firm*—Sprung, Horn, Kramer & Woods

[57] ABSTRACT

The present invention provides aminopropanol derivatives of the general formula:

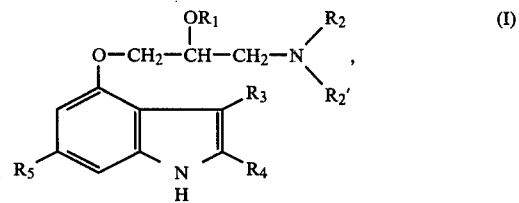

wherein $R_1$ is a hydrogen atom or a lower alkanoyl or an aroyl radical, $R_2$ is a lower alkyl radical or a radical of the general formula:

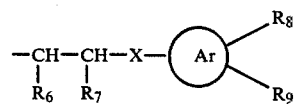

wherein X is a valency bond, a methylene group or an oxygen or sulphur atom, Ar is a monocyclic, carbo- or heterocyclic aryl radical, $R_6$ and $R_7$, which can be the same or different, are hydrogen atoms or lower alkyl radicals, $R_8$ and $R_9$, which can be the same or different, are hydrogen or halogen atoms, hydroxyl groups, lower alkanoyl radicals, alkenyl radicals, alkynyl radicals, alkyl radicals, lower alkoxy radicals, aralkoxy radicals, alkenyloxy radicals, alkynyloxy radicals, lower alkylthio radicals, aminocarbonyl radicals, aminosulphonyl radicals or acylamino radicals; or $R_2$ is a 1,4-benzodioxan-2-ylmethyl radical, $R'_2$ is a hydrogen atom or a benzyl radical, $R_3$ is a carboxyl group or a lower alkoxycarbonyl, aminocarbonyl, cyano, oximinomethyl, formyl, hydroxymethyl or lower alkoxycarbimidoyl radical, $R_4$ is a hydrogen atom or a lower alkyl radical or a —CH$_2$—O—R$_1$ radical, $R_1$ having the same meaning as above, and $R_5$ is a hydrogen atom or a lower alkyl radical; the optionally-active forms and racemates thereof and the pharmacologically acceptable salts thereof. The present invention also provides processes for the preparation of these compounds and pharmaceutical compositions containing them. Furthermore, the present invention is concerned with the use of these compounds for the prophylaxis and treatment of heart and circulatory diseases.

8 Claims, No Drawings

3-CYANO-INDOLES AS CARDIOSELECTIVE AGENTS

The present invention is concerned with new aminopropanol derivatives, with processes for the preparation thereof and with pharmaceutical compositions containing these new derivatives.

The new aminopropanol derivatives according to the present invention are compounds of the general formula:

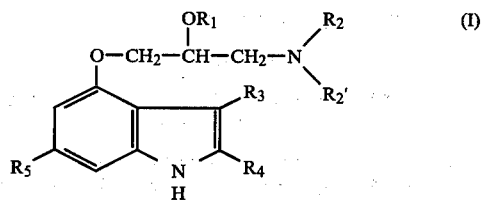

wherein $R_1$ is a hydrogen atom or a lower alkanoyl or an aroyl radical, $R_2$ is a lower alkyl radical or a group of the general formula:

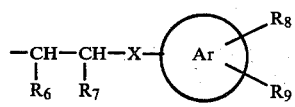

wherein X is a valency bond, a methylene group or an oxygen or sulphur atom, Ar is a monocyclic, carbo- or heterocyclic aryl radical, $R_6$ and $R_7$, which can be the same or different, are hydrogen atoms or lower alkyl radicals, $R_8$ and $R_9$, which can be the same or different, are hydrogen or halogen atoms, hydroxyl groups, lower alkanoyl radicals, alkenyl radicals, alkynyl radicals, alkyl radicals, lower alkoxy radicals, aralkoxy radicals, alkenyloxy radicals, alkynyloxy radicals, alkylthio radicals, aminocarbonyl radicals, aminosulphonyl radicals or alkanoyl radicals, or $R_2$ is a 1,4-benzodioxan-2-ylmethyl radical, $R'_2$ is a hydrogen atom or a benzyl radical, $R_3$ is a carboxyl group or a lower alkoxycarbonyl, aminocarbonyl, cyano, oximinomethyl, formyl, hydroxymethyl or lower alkoxycarbimidoyl radical, $R_4$ is a hydrogen atom or a lower alkyl radical or a —CH$_2$—O—$R_1$ radical, wherein $R_1$ has the same meaning as above, and $R_5$ is a hydrogen atom or a lower alkyl radical; and the pharmacologically acceptable salts thereof.

Since the compounds of general formula (I) possess an asymmetric carbon atom, the present invention also includes within its scope the optically-active forms and the racemic mixtures of these compounds.

Indole derivatives substituted in the 2-position and of similar structure are described in published Federal Republic of Germany Patent Specification No. 28 30 211.

Suprisingly, we have found that the compounds of general formula (I) substituted in the 3-position, as well as their pharmacologically acceptable salts, show, in contradistinction to the above-mentioned known compounds, an outstanding inhibition of the $\beta_1$-receptors, i.e. they are cardioselective. Therefore, they are suitable for the treatment and prophylaxis of heart and circulatory diseases.

The lower alkanoyl radicals in the definition of the substituents $R_1$, $R_8$ and $R_9$ are to be understood to be straight-chained or branched radicals containing up to 6 and preferably up to 5 carbon atoms, the formyl, acetyl and pivaloyl radicals being preferred.

The aroyl radical in the definition of $R_1$ is to be understood to be a benzoyl radical which can be substituted one or more times by halogen, nitro, alkyl containing up to 4 carbon atoms or alkoxy containing up to 4 carbon atoms.

The lower alkyl radicals in the definition of the substituents $R_2$, $R_4$, $R_5$, $R_6$, $R_7$, $R_8$ and $R_9$ are straight-chained or branched radicals containing up to 6 and preferably up to 4 carbon atoms, for example, methyl, ethyl, n-propyl, isopropyl, n-butyl, isobutyl, tert.-butyl or n-hexyl radicals, the methyl, ethyl, isopropyl and tert.-butyl radicals being especially preferred.

The monocyclic carbo- or heterocyclic aryl radicals $R_2$ are to be understood to be radicals such as the phenyl, pyridyl, furyl, pyrimidyl, pyridazinyl and thienyl radicals, the phenyl radical being especially preferred.

The alkenyl and alkynl radicals in the definition of $R_8$ and $R_9$ contain 2 to 6 and preferably 2 to 4 carbon atoms, the allyl and propargyl radicals being preferred.

The alkoxy radicals in the definition of $R_8$ and $R_9$ contain up to 6 and preferably up to 4 carbon atoms, for example methoxy, ethoxy, propoxy, butoxy and pentoxy radicals, the methoxy, ethoxy and propoxy radicals being preferred.

The alkenyloxy and alkynyloxy radicals in the definition of $R_8$ and $R_9$ contain up to 6 and preferably up to 4 carbon atoms, the allyloxy and propargyloxy radicals being preferred.

As alkoxycarbonyl radicals in the definition of $R_3$, the methoxycarbonyl and ethoxycarbonyl radicals are especially preferred.

The lower alkoxycarbimidoyl radicals in the definition of $R_3$ are preferably the methoxycarbimidoyl and ethoxycarbimidoyl radicals.

The alkylthio and alkanoylamino radicals in the definition of $R_8$ and $R_9$ contain up to 6 and preferably up to 4 carbon atoms, the methylthio and acetylamino radical being preferred.

The halogen atoms are to be understood to be fluorine, chlorine, bromine and iodine atoms, fluorine, chlorine and bromine atoms being preferred.

The compounds of general formula (I) can be prepared, for example, by reacting a compound of the general formula:

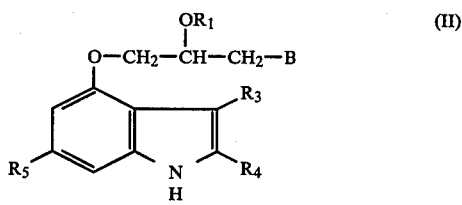

wherein $R_1$, $R_3$, $R_4$ and $R_5$ have the same meanings as above and B is a reactive group or, together with $R_1$, represents a valency bond, with a compound of the general formula:

wherein $R_2$ and $R'_2$ have the same meanings as above, and possibly subsequently, in a compound obtained of general formula (I), one of the substituents $R_1$, $R'_2$, $R_3$, $R_4$ or $R_5$ is converted by known methods into a different substituent $R_1$, $R'_2$, $R_3$, $R_4$ or $R_5$ of the above-given meaning and the compounds obtained are, if desired, converted into their pharmacologically acceptable salts.

Reactive groups in compounds of general formula (II) are, in particular, acid residues of, for example, hydrohalic acids or sulphonic acids, preferred reactive groups being chloride, mesyloxy and tosyloxy radicals.

The compounds of general formula (II) can be prepared by the processes described in the application Ser. No. 288,077 now U.S. Pat. No. 4,442,295 filed concurrently herewith and corresponding to Federal Republic of Germany Patent Specification No. 30 29 980.10.

The reactions can be carried out without the use of a solvent or can be carried out in a solvent, for example methanol, ethanol, n-butanol, diethyl ether, methylene chloride, chloroform, benzene, toluene, ethyl acetate, tetrahydrofuran or dioxane, especially preferred solvents being methanol, ethanol and n-butanol.

Conversions of one of the substituents $R_1$, $R'_2$, $R_3$, $R_4$ or $R_5$ in compounds of general formula (I) which can possibly be carried out subsequently into other substituents $R_1$, $R'_2$, $R_3$, $R_4$ or $R_5$ include, for example: the dehydration of an aminocarbonyl or oximinomethyl radical to give a cyano group; the reduction of a formyl radical to give a hydroxymethyl radical; the conversion of a formyl radical into an oximinomethyl radical by reaction with hydroxylamine.

The compounds of general formula (I) according to the present invention can be obtained in the form of a racemic mixture. The separation of the racemates into the optically-active form is carried out by known methods via diastereomeric salts of active acids, for example tartaric acid, malic acid or camphorsulphonic acid.

For the conversion of the compounds of general formula (I) into their pharmacologically acceptable salts, they are reacted, preferably in an organic solvent, with an equivalent amount of an inorganic or organic acid, for example hydrochloric acid, hydrobromic acid, phosphoric acid, sulphuric acid, acetic acid, citric acid, maleic acid, benzoic acid or the like.

For the preparation of pharmaceutical compositions, the compounds (I) are mixed in known manner with appropriate pharmaceutical carrier materials and aroma, flavoring and coloring materials and shaped, for example, into tablets or dragees or, with the addition of appropriate adjuvants, suspended or dissolved in water or in an oil, for example olive oil.

The new compounds (I) according to the present invention and the salts thereof can be administered enterally or parenterally in liquid or solid form. As injection medium, it is preferable to use water which contains the usual an oil, for exajection solutions, such as stabilizing agents, solubilizing agents or buffers.

Additives of this kind include, for example, tartrate and citrate buffers, ethanol, complex formers (such as ethylenediamine-tetraacetic acid and the nontoxic salts thereof) and high molecular weight polymers (such as liquid polyethylene oxide) for viscosity regulation. Solid carrier materials include, for example, starch, lactose, mannitol, methyl cellulose, talc, highly-dispersed silicic acids, high molecular weight fatty acids (such as stearic acid), gelatine, agar agar, calcium phosphate, magnesium stearate, animal and vegetable fats and solid high molecular weight polymers (such as polyethylene glycols). Compositions suitable for oral administration can, if desired, contain flavoring and/or sweetening agents.

Preferred compounds according to the present invention, apart from those described in the following examples, include the following:
4-[2-hydroxy-3-(benzo[b]-1,4-dioxan-2-ylmethylamino)-propoxy]-3-cyanoindole,
4-{2-hydroxy-3-[2-(2-methoxyphenoxy)-ethylamino]-propoxy}-2-methyl-3-cyanoindole,
4-{2-hydroxy-3-[2-(2-allyloxyphenoxy)-ethylamino]-propoxy}-2-methyl-3-cyanoindole, and
4-{2-hydroxy-3-[2-(2-acetamidophenoxy)-ethylamino]-propoxy}-2-methyl-3-cyanoindole.

The following examples are given for the purpose of illustrating the present invention:

EXAMPLE 1

4-[2-Hydroxy-3-(N-benzylisopropylamino)-propoxy]-3-formylindole.

3.5 g. 4-(2,3-Epoxypropoxy)-3-formylindole are dissolved in 50 ml. n-butanol, 3.6 g. N-benzylisopropylamine are added thereto and the reaction mixture is boiled for 24 hours. After cooling, the reaction mixture is filtered with suction. There are obtained 3.8 g. (64% of theory) 4-[2-hydroxy-3-(N-benzylisopropylamino)-propoxy]-3-formylindole; m.p. 107°–109° C.

EXAMPLE 2

4-[2-Hydroxy-3-(isopropylamino)-propoxy]-3-hydroxymethylindole 8.4 g. 4-(2,3-Epoxypropoxy)-3-hydroxymethylindole are stirred for 18 hours with 50 ml. isopropylamine. The reaction mixture is then evaporated in a vacuum and the residue is taken up in ethyl acetate to which the equivalent amount of benzoic acid is added to give 4-[2-hydroxy-3-(isopropylamino)-propoxy]-3-hydroxymethylindole benzoate. After recrystallization from methanol, the yield is 3.3 g. (22% of theory); m.p. 141° C.

EXAMPLE 3

4-[2-Hydroxy-3-(isopropylamino)-propoxy]-3-ethoxycarbonylindole 11.5 g. 4-(2,3-Epoxypropoxy)-3-ethoxycarbonylindole are stirred for 10 hours with 70 ml. isopropylamine. The reaction mixture is then evaporated in a vacuum and the residue shaken up with 1N lactic acid and diethyl ether. The aqueous phase is mixed with potassium carbonate, the precipitated base is taken up in ethyl acetate/diethyl ether and, after drying over anhydrous sodium sulphate and evaporation of the solvent, there are obtained 10.9 g. 4-[2-hydroxy-3-(isopropylamino)-propoxy-]-3-ethoxycarbonylindole. The base is dissolved in ethyl acetate, mixed with the equivalent amount of benzoic acid and filtered with suction. There are obtained 10.1 g. (52% of theory) of the corresponding benzoate; m.p. 191° C.

The following compounds are obtained in an analogous manner:

| | designation | Yield % | m.p. °C. (solvent) |
|---|---|---|---|
| (a) | 4-[2-hydroxy-3-(isopropylamino)-propoxy]-3-aminocarbonylindole benzoate from 4-(2,3-epoxypropoxy)-3-aminocarbonylindole and isopropylamine | 25 | 150–152 (isopropanol) |
| (b) | 4-[2-hydroxy-3-(isopropylamino)- | 25 | 145–147 |

-continued

| | designation | Yield % | m.p. °C. (solvent) |
|---|---|---|---|
| | propoxy]-3-cyanoindole benzoate from 4-(2,3-epoxypropoxy)-3-cyanoindole and isopropylamine | | (ethyl acetate) |
| (c) | 4-[2-hydroxy-3-(isopropylamino)-propoxy]-2-hydroxymethyl-3-indole from 4-(2,3-epoxypropoxy)-2-acetoxymethyl-3-cyanoindole and isopropylamine | 66 | 178–179 (ethyl acetate) |
| (d) | 4-[2-hydroxy-3-(isopropylamino)-propoxy]-2-methyl-3-cyanoindole from 4-(2,3-epoxypropoxy)-2-methyl-3-cyanoindole and isopropylamine | 70 | 153 (diethyl ether) |
| (e) | 4-[hydroxy-3-(isopropylamino)-propoxy]-3-cyano-6-methylindole benzoate from 4-(2,3-epoxypropoxy)-3-cyano-6-methylindole and isopropylamine | 27 | 189–191 (ethyl acetate) |
| (f) | 4-[2-hydroxy-3-(isopropylamino)-propoxy]-3-cyano-6-tert.-butylindole from 4-(2,3-epoxypropoxy)-3-cyano-6-tert.-butylindole and isopropylamine | | |
| (g) | 4-{2-hydroxy-3-[2-(2-methoxyphenoxy)-ethylamino]-propoxy}-3-cyanoindole benzoate from 4-(2,3-epoxypropoxy)-3-cyanoindole and 2-(2-methoxyphenoxy)-ethylamine | 20 | 117–113 (ethyl acetate) |
| (h) | 4-{2-hydroxy-3-[2-(2-allyloxyphenoxy)-ethylamino]-propoxy}-3-cyanoindole benzoate from 4-(2,3-epoxypropoxy)-3-cyanoindole and 2-(2-allyloxyphenoxy)-ethylamine | 22 | 125–127 (ethyl acetate) |
| (i) | 4-{2-hydroxy-3-[2-(2-hydroxyphenoxy)-ethylamino]-propoxy}-3-cyanoindole benzoate from 4-(2,3-epoxypropoxy)-3-cyanoindole and 2-(2-hydroxyphenoxy)-ethylamine | 20 | 147–149 (ethyl acetate) |
| (j) | 4-{2-hydroxy-3-[2-(3,4-dimethoxyphenyl)-ethylamino]-propoxy}-3-cyanoindole benzoate from 4-(2,3-epoxypropoxy)-3-cyanoindole and 2-(3,4-dimethoxyphenyl)-ethylamine | 25 | 142–143 (ethyl acetate) |
| (k) | 4-{2-hydroxy-3-[2-(4-hydroxyphenyl)-ethylamino]-propoxy}-3-cyanoindole p-nitrobenzoate from 4-(2,3-epoxypropoxy)-3-cyanoindole and 2-(4-hydroxyphenyl)-ethylamine | 25 | 183 (methanol) |
| (l) | 4-{2-hydroxy-3-[2-(2-allyloxyphenyl)-ethylamino]-propoxy}-3-cyanoindole from 4-(2,3-epoxypropoxy)-3-cyanoindole and 2-(2-allyloxyphenyl)-ethylamine | 40 | 154–155 (isopropanol) |
| (m) | 4-{2-hydroxy-3-[2-(2-allyloxyphenoxy)-ethylamino]-propoxy}-3-cyano-6-tert.-butylindole from 4-(2,3-epoxypropoxy)-3-cyano-6-tert.-butylindole and 2-(2-allyloxyphenoxy)-ethylamine | 50 | 114–116 (ethyl acetate diethyl ether) |
| (n) | 4-{2-hydroxy-3-[2-(4-hydroxyphenoxy)-ethylamino]-propoxy}-3-cyanoindole from 4-(2,3-epoxypropoxy)-3-cyanoindole and 2-(4-hydroxyphenoxy)-ethylamine | 30 | 117–119 (methanol) |
| (o) | 4-[2-hydroxy-3-(2-phenoxyethylamino)-propoxy]-3-cyanoindole from 4-(2,3-epoxypropoxy)-3-cyanoindole and 2-phenoxyethylamine | 50 | 160–162 (methanol) |
| (p) | 4-{2-hydroxy-3-[2-(4-carbamidophenoxy)-ethylamino]-propoxy}-3-cyanoindole from 4-(2,3-epoxypropoxy)-3-cyanoindole and 2-(4-carbamidophenoxy)-ethylamine | 20 | 185 (methanol) |
| (q) | 4-{2-hydroxy-3-[2-(2-methylthiophenoxy)-ethylamino]-propoxy}-3-cyanoindole from 4-(2,3-epoxypropoxy)-3-cyanoindole and 2-(2-methylthiophenoxy)-ethylamine | 60 | 179–181 (ethylene glycol dimethyl ether) |

EXAMPLE 4

4-[2-hydroxy-3-(isopropylamino)-propoxy]-3-formylindole benzoate.

6.6 g. 4-[2-hydroxy-3-(N-benzylisopropylamino)-propoxy]-3-formylindole (see Example 1) are dissolved in 150 ml. methanol, mixed with 0.5 g. 10% palladium-charcoal and hydrogenated at ambient temperature and under a hydrogen pressure of 1 bar. The reaction mixture is subsequently filtered and concentrated to a volume of about 20 ml. and the equivalent amount of benzoic acid is added thereto. After suction filtration, there are obtained 3.1 g. (44% of theory) 4-[2-hydroxy-3-(isopropylamino-propoxy]-3-formylindole benzoate; m.p. 204°–105° C.

EXAMPLE 5

4-[2-hydroxy-3-(isopropylamino)-propoxy]-3-oximinomethylindole benzoate 5.7 g. 4-[2-hydroxy-3-(isopropylamino)-propoxy]-3-formylindole are dissolved in 30 ml. ethanol and 30 ml. water, mixed with 2.2 g. sodium acetate and 1.1 g. hydroxylamine hydrochloride and stirred for 2 hours at ambient temperature. After evaporating off the alcohol in a vacuum, the residue is taken up in ethyl acetate and the ethyl acetate phase is mixed with the equivalent amount of benzoic acid, there thus being obtained 3.3 g. (55% of theory) 4-[2-hydroxy-3-(isopropylamino)-propoxy]-3-oximinomethylindole benzoate; m.p. 208°–210° C.

EXAMPLE 6

Tablets are prepared, each of which contains 50 mg. 4-[2-hydroxy-3-(isopropylamino)-propoxy]-3-cyanindole benzoate The tablets are prepared according to the following formulation:

| | |
|---|---|
| 4-[2-hydroxy-3-(isopropylamino)-propoxy-]-3-cyanoindole benzoate | 50 g. |
| lactose | 80 g. |

| | |
|---|---|
| starch | 29 g. |
| magnesium stearate | 1 g. |

The active compound is finely powdered and mixed with the lactose and starch. The mixture is then granulated in the usual manner, magnesium stearate is added to the granulate and the mixture is pressed to give 1000 tablets, each with a weight of 0.16 g.

The formulation and dosage of the novel compounds is similar to that of other β-receptor inhibitors. The actual dosage schedule for inhibition of β-receptors is dependent on the condition of the patient, e.g. a human or animal mammal, his response to the treatment and whether or not he is ambulatory or hospitalized. The treatment should be begun with small doses (100 mg) and increased gradually depending upon the patient's response. The dosage can be increased at 5 to 7 day intervals until an average daily dose of 100 to 300 mg is reached. For maintenance, two to four doses a day are usually required.

In order to establish the effectiveness of the novel products of the invention a series of tests was carried out as follows:

Test Protocol

Beta-blockers are characterized pharmacologically in that they block the isoprenaline effect. This relates to the isoprenaline tachycardia (=beta$_1$-effect) on the one hand, and to the isoprenaline-induced slackening of the smooth musculature which corresponds to a vasodilation, blood pressure drop and a bronchodilation (=beta$_2$-effect) on the other hand. It is desired, however, that there is exhibited only the beta-blocker-induced inhibition of isoprenaline tachycardia which, therapeutically, corresponds to a prevention of a rise in heart beat during physical and psychic stresses, whereas the isoprenaline effect on the smooth musculature, notwithstanding the beta-blocker pressure, is desirably unchanged insofar as possible. Such an activity spectrum of a beta-blocker is termed cardioselective.

In an animal experiment, that dose of the beta-blocker is sought which will limit the isoprenaline effect on the smooth musculature (=vasodilation and/or lowering of blood pressure) on the one hand, and limit to half (=HD$_{50}$) the heart beat rise on the other hand.

If the quotient HD$_{50}$% lowering of blood pressure to HD$_{50}$% frequency is high, it means that for inhibiting isoprenaline tachycardia relatively small doses of the beta-blocker are required, while for inhibiting the effect on the smooth musculature high doses are required, that thus the beta-blocker has cardioselective properties. Thus the higher the quotient, the more cardioselective is the substance.

Test procedure:

Rabbits are placed in wooden cages and a catheter inserted under local anaesthesia into the middle ear artery. Over an electromechanical pressure transformer, the blood pressure is measured continuously and, from it, at a fast paper advance, the heart rate calculated. Over an ear vein, first 1ug/kg isoprenaline is injected i.v., which causes a diastolic drop in blood pressure of about 40 mm Hg and results in a heart beat rise from about 210 to 320 beats/minute. After this control injection, the dissolved test substances of the beta-blockers are administered intravenously in increasing doses at intervals of 10 minutes (doses: 0.125+0.125+0.25+0.5+1.0+2.0+4.0 mg/kg i.v.), and then each time the isoprenaline effect is determined anew. Both for the isoprenaline effect on the blood pressure and on the heart beat frequency that dose of the beta-blocker is extrapolated which limits to half (=HD$_{50}$) the isoprenaline effect.

Results:

In the table below, the test results for the compounds of the invention are summarized.

As comparison substances, there were employed the following two representative compounds from German Offenlegungsschrift 28 30 211:

(A) 4-[2-hydroxy-3-(isopropylamino)propoxy]-2cyanoindole (Position isomer of Example 3b of instant specification covered by the claim of German Offenlegungsschrift No. 28 30 211)

(B) 4-[2-hydroxy-3(t-butylamino)-propoxy]-2-cyanoindole (Example 2 of German Offenlegungsschrift 28 30 211).

The absolute effective doses of the beta-blockers are not important for assessing the performance of the substances, only the indicated quotients are of importance.

All data given in the table below are the mean values of 6 individual tests.

TABLE

Inhibiting doses of beta-blockers vis-a-vis the blood pressure lowering and/or frequency-raising effect of 1 μg/kg isoprenaline

| Active Material | HD$_{50}$% bl. (μg/kg i.v.) | HD$_{50}$% fr. (μg/kg i.v.) | Cardioselectivity quotient |
|---|---|---|---|
| A | 2.1 | 1.5 | 1.4 |
| B | 2.6 | 2.6 | 1.0 |
| Ex. 3b | 34 | 5.5 | 6.2 |
| Ex. 3c | 3.2 | 7.1 | 0.45 |
| Ex. 3d | 2.5 | 3.8 | 0.7 |
| Ex. 3e | 12 | 9.0 | 1.3 |
| Ex. 3g | 509 | 82 | 6.2 |
| Ex. 3h | 1143 | 209 | 5.5 |
| Ex. 3i | 34 | 18 | 1.9 |
| Ex. 3j | 521 | 71 | 7.3 |
| Ex. 3k | 201 | 137 | 1.5 |
| Ex. 3n | 183 | 23 | 8.0 |
| Ex. 3o | 192 | 53 | 3.6 |
| Ex. 3p | 343 | 89 | 3.9 |

It will be appreciated that the instant specification and examples are set forth by way of illustration and not limitation, and that various modifications and changes may be made without departing from the spirit and scope of the present invention.

I claim:

1. An aminopropanol of the formula

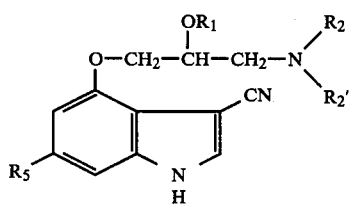

in which

R$_1$ is a hydrogen atom, a C$_{1-6}$-alkanoyl radical or a benzoyl radical optionally substituted by halogen, nitro, C$_{1-4}$-alkyl or C$_{1-4}$-alkoxy radical, R$_2$ is a C$_{1-6}$-alkyl radical or a radical of the formula

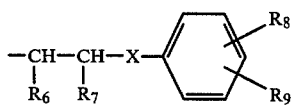

X is a valency bond, a methylene group or an oxygen atom, $R_6$ and $R_7$ each independently is a hydrogen atom or a $C_{1-6}$-alkyl radical, $R_8$ and $R_9$ each independently is a hydrogen or halogen atom, or a hydroxyl, $C_{1-6}$-alkyl, $C_{1-6}$-alkoxy, or $C_{2-6}$-alkenyloxy radical or one of them is an aminocarbonyl radical, $R'_2$ is a hydrogen atom or a benzyl radical, $R_5$ is a hydrogen atom or a $C_{1-6}$-alkyl radical, or a pharmacologically acceptable salt thereof.

2. A compound according to claim 1, wherein such compound is 4-[2-hydroxy-3-(isopropylamino)-propoxy]-3-cyanoindole or a pharmacologically acceptable salt thereof.

3. A compound according to claim 1, wherein such compound is 4-{2-hydroxy-3-[2-(2-methoxy-phenoxy)-ethylamino]-propoxy}-3-cyanoindole or a pharmacologically acceptable salt thereof.

4. A compound according to claim 1, wherein such compound is 4-{2-hydroxy-3-[2-(2-allyloxy-phenoxy)-ethylamino]-propoxy}-3-cyanoindole or a pharmacologically acceptable salt thereof.

5. A compound according to claim 1, wherein such compound is 4-{2-hydroxy-3-[2-(3,4-dimethoxyphenyl)-ethylamino]-propoxy}-3-cyanoindole or a pharmacologically acceptable salt thereof.

6. A compound according to claim 1, wherein such compound is 4-{2-hydroxy-3-[2-(4-hydroxy-phenoxy)-ethylamino]-propoxy}-3-cyanoindole or a pharmacologically acceptable salt thereof.

7. A $\beta$-receptor inhibiting composition of matter comprising a $\beta$-receptor inhibiting amount of a compound or salt according to claim 1 in admixture with a pharmacologically acceptable diluent.

8. The method of inhibiting the $\beta$-receptors of a patient which comprises administering to said patient $\beta$-receptor inhibiting amount of a compound or salt according to claim 1.

* * * * *